US009610347B2

(12) United States Patent
Menear et al.

(10) Patent No.: US 9,610,347 B2
(45) **Date of Patent: *Apr. 4, 2017**

(54) VACCINATION RESPONSE FOR IMMUNODEFICIENCY OR HIGH CORTISOL

(71) Applicant: CortControl, Santa Cruz, CA (US)

(72) Inventors: John Edgar Menear, Santa Cruz, CA (US); Joseph Ramaekers, Aptos, CA (US)

(73) Assignee: CortControl, Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,457

(22) Filed: Mar. 6, 2015

(65) Prior Publication Data

US 2015/0174241 A1 Jun. 25, 2015

Related U.S. Application Data

(60) Continuation-in-part of application No. 13/877,309, filed on Jun. 3, 2013, which is a continuation-in-part of application No. 12/631,745, filed on Dec. 4, 2009, now abandoned, said application No. 12/631,745 is a continuation of application No. 11/492,464, filed on Jul. 24, 2006, now abandoned, and a continuation-in-part of application No. 11/106,054, filed on Apr. 13, 2005, now abandoned, said application No. 12/631,745 is a continuation of application No. 11/237,316, filed on Sep. 27, 2005, now abandoned, which is a division of application No. 10/136,854, filed on Apr. 30, 2002, now Pat. No. 6,962,718, which is a continuation-in-part of application No. 09/847,036, filed on Apr. 30, 2001, now Pat. No. 6,506,413.

(60) Provisional application No. 61/389,190, filed on Oct. 1, 2010, provisional application No. 61/389,230, filed on Oct. 2, 2010, provisional application No. 60/701,860, filed on Jul. 22, 2005, provisional application No. 60/573,113, filed on May 20, 2004, provisional application No. 60/649,363, filed on Feb. 1, 2005.

(51) Int. Cl.

| | |
|---|---|
| ***A61K 35/74*** | (2015.01) |
| ***A61K 39/39*** | (2006.01) |
| ***A61K 39/02*** | (2006.01) |
| ***A61K 39/12*** | (2006.01) |
| *A61K 39/00* | (2006.01) |
| *A61K 35/744* | (2015.01) |

(52) U.S. Cl.

CPC .......... *A61K 39/39* (2013.01); *A61K 39/0225* (2013.01); *A61K 39/12* (2013.01); *A61K 35/744* (2013.01); *A61K 2039/55516* (2013.01); *A61K 2039/55594* (2013.01); *C12N 2750/14334* (2013.01); *C12N 2760/20134* (2013.01)

(58) Field of Classification Search

CPC ................................ A61K 35/744; C12R 1/01

See application file for complete search history.

(56) References Cited

U.S. PATENT DOCUMENTS

| | | | |
|---|---|---|---|
| 2004/0029127 A1* | 2/2004 | Postaire ............... | A23C 9/1234 435/6.11 |
| 2007/0053919 A1* | 3/2007 | Lisonbee ................ | A61J 3/074 424/184.1 |

OTHER PUBLICATIONS

U.S. Appl. No. 13/877,309.*

* cited by examiner

*Primary Examiner* — Ruth Davis

(74) *Attorney, Agent, or Firm* — Schwabe, Williamson & Wyatt, P.C.

(57) ABSTRACT

A method of improving a human's response to vaccination with a vaccine enhancing food. This food contains at least transfer factor and lactic acid generating bacteria, and in some embodiments includes glucans. The vaccine enhancing food may be consumed before, during, or after the vaccination. The results are an improvement in the vaccine titer, a slower decay of titer, longer periods of immunity, and fewer needed boosters.

11 Claims, 3 Drawing Sheets

Figure 1 – Immune Response Comparison from Lisonbee U.S. 6,468,534 Demonstrating No Vaccine Enhancement for Hepatitis B

TABLE 6

Hepatitis B Vaccine - First Test Population (Antibody and Transfer Factor Administered)

| | Footpad size (μm) | | |
|---|---|---|---|
| | Before Sample Injection (0 hrs.) | Final (24 hrs.) | Difference |
| Mouse #1 | | | |
| Left Foot (Control) | 2032.00 | 2108.20 | 76.20 |
| Right Foot (Test) | 2032.00 | 2082.80 | 50.80 |
| Mouse #2 | | | |
| Left Foot (Control) | 2260.60 | 2362.20 | 101.60 |
| Right Foot (Test) | 2209.80 | 2336.80 | 127.00 |
| Mouse #3 | | | |
| Left Foot (Control) | 2159.00 | 2184.40 | 25.40 |
| Right Foot (Test) | 2159.00 | 2235.20 | 76.20 |
| Mouse #4 | | | |
| Left Foot (Control) | 2108.20 | 2184.40 | 76.20 |
| Right Foot (Test) | 2108.20 | 2260.60 | 152.40 |
| Mouse #5 | | | |
| Left Foot (Control) | 1930.40 | 2032.00 | 101.60 |
| Right Foot (Test) | 1930.40 | 2108.20 | 177.80 |
| Mouse #6 | | | |
| Left Foot (Control) | 2184.40 | 2184.40 | 0.00 |
| Right Foot (Test) | 2184.40 | 2235.20 | 50.80 |

TABLE 7

Hepatitis B Vaccine - Second Test Population (Only Transfer Factor Administered)

| | Footpad size (μm) | | |
|---|---|---|---|
| | Before Sample Injection (0 hrs.) | Final (24 hrs.) | Difference |
| Mouse #1 | | | |
| Left Foot (Control) | 1981.20 | 2032.00 | 50.80 |
| Right Foot (Test) | 2006.60 | 2159.00 | 152.40 |
| Mouse #2 | | | |
| Left Foot (Control) | 1981.20 | 1981.20 | 0.00 |
| Right Foot (Test) | 1981.20 | 2006.60 | 25.40 |
| Mouse #3 | | | |
| Left Foot (Control) | 2006.60 | 2032.00 | 25.40 |
| Right Foot (Test) | 2032.00 | 2082.80 | 50.80 |

TABLE 7-continued

Hepatitis B Vaccine - Second Test Population (Only Transfer Factor Administered)

| | Footpad size (μm) | | |
|---|---|---|---|
| | Before Sample Injection (0 hrs.) | Final (24 hrs.) | Difference |
| Mouse #4 | | | |
| Left Foot (Control) | 1955.80 | 2133.60 | 177.80 |
| Right Foot (Test) | 1981.20 | 2108.20 | 127.00 |
| Mouse #5 | | | |
| Left Foot (Control) | 1930.40 | 2006.60 | 76.20 |
| Right Foot (Test) | 1930.40 | 2057.40 | 127.00 |
| Mouse #6 | | | |
| Left Foot (Control) | 2032.00 | 2057.40 | 25.40 |
| Right Foot (Test) | 2006.60 | 2108.20 | 101.60 |

Mean difference = 0.0

Student's t Test confirms no difference

| Mouse number | Right mouse pad for transfer factor plus vaccine (from Lisonbee table 6) | Right mouse pad for transfer factor alone (from Lisonbee table 7) |
|---|---|---|
| 1 | 50.80 | 152.40 |
| 2 | 127.00 | 25.40 |
| 3 | 76.20 | 50.80 |
| 4 | 152.40 | 177.80 |
| 5 | 177.80 | 127.00 |
| 6 | 50.80 | 101.60 |

Figure 2 – Immune Response Comparison from Lisonbee U.S. 6,468,534 Demonstrating No Vaccine Enhancement for H. Pylori

TABLE 10

*H. Pylori* - First Test Population (Antibody and Transfer Factor Administered)

| | Footpad size (µm): Before Sample Injection (0 hrs.) | Final (24 hrs.) | Difference |
|---|---|---|---|
| Mouse #1 | | | |
| Left Foot (Control) | 1955.80 | 1981.20 | 25.40 |
| Right Foot (Test) | 1930.40 | 1955.80 | 25.40 |
| Mouse #2 | | | |
| Left Foot (Control) | 2133.60 | 2133.60 | 0.00 |
| Right Foot (Test) | 2108.20 | 2260.60 | 152.40 |
| Mouse #3 | | | |
| Left Foot (Control) | 2082.80 | 2082.80 | 0.00 |
| Right Foot (Test) | 2108.20 | 2133.60 | 25.40 |
| Mouse #4 | | | |
| Left Foot (Control) | 2082.80 | 2184.40 | 101.60 |
| Right Foot (Test) | 2082.80 | 2286.00 | 203.20 |
| Mouse #5 | | | |
| Left Foot (Control) | 2108.20 | 2133.60 | 25.40 |
| Right Foot (Test) | 2133.60 | 2133.60 | 0.00 |
| Mouse #6 | | | |
| Left Foot (Control) | 1955.80 | 2032.00 | 76.20 |
| Right Foot (Test) | 1930.40 | 2108.20 | 177.80 |

TABLE 11

*H. Pylori* - Second Test Population (Only Transfer Factor Administered)

| | Footpad size (µm): Before Sample Injection (0 hrs.) | Final (24 hrs.) | Difference |
|---|---|---|---|
| Mouse #1 | | | |
| Left Foot (Control) | 2235.20 | 2235.20 | 0.00 |
| Right Foot (Test) | 2184.40 | 2209.80 | 25.40 |
| Mouse #2 | | | |
| Left Foot (Control) | 2006.60 | 2006.60 | 0.00 |
| Right Foot (Test) | 2006.60 | 2032.00 | 25.40 |
| Mouse #3 | | | |
| Left Foot (Control) | 2082.80 | 2184.40 | 101.60 |
| Right Foot (Test) | 2133.60 | 2209.80 | 76.20 |
| Mouse #4 | | | |
| Left Foot (Control) | 2133.60 | 2133.60 | 0.00 |
| Right Foot (Test) | 2133.60 | 2159.00 | 25.40 |
| Mouse #5 | | | |
| Left Foot (Control) | 2159.00 | 2184.40 | 25.40 |
| Right Foot (Test) | 2159.00 | 2235.20 | 76.20 |
| Mouse #6 | | | |
| Left Foot (Control) | 2057.40 | 2082.80 | 25.40 |
| Right Foot (Test) | 2032.00 | 2260.60 | 228.60 |

Mean difference = 19.5

Student's t Test shows a 70% chance that means are not different.

| Mouse number | Right mouse pad for transfer factor plus vaccine (from Lisonbee table 10) | Right mouse pad for transfer factor alone (from Lisonbee table 11) |
|---|---|---|
| 1 | 25.40 | 25.40 |
| 2 | 152.40 | 25.40 |
| 3 | 25.40 | 76.20 |
| 4 | 203.20 | 25.40 |
| 5 | 0.00 | 76.20 |
| 6 | 177.80 | 238.60 |

Figure 3 – Immune Response Comparison from Lisonbee U.S. 6,468,534 Demonstrating No Vaccine Enhancement for EBV EBNA-1

TABLE 14

EBV EBNA-1 - First Test Population
(Arthrodyzed Transfer Factor Administered)

| | Footpad size (μm): | | |
|---|---|---|---|
| | Before Sample Injection (0 hrs.) | Final (24 hrs.) | Difference |
| Mouse #1 | | | |
| Left Foot (Control) | 2032.00 | 2057.40 | 25.40 |
| Right Foot (Test) | 2032.00 | 2057.40 | 25.40 |
| Mouse #2 | | | |
| Left Foot (Control) | 2159.00 | 2159.00 | 0.00 |
| Right Foot (Test) | 2159.00 | 2184.40 | 25.40 |
| Mouse #3 | | | |
| Left Foot (Control) | 2159.00 | 2159.00 | 0.00 |
| Right Foot (Test) | 2133.60 | 2286.00 | 152.40 |
| Mouse #4 | | | |
| Left Foot (Control) | 2108.20 | 2108.20 | 0.00 |
| Right Foot (Test) | 2108.20 | 2209.80 | 101.60 |
| Mouse #5 | | | |
| Left Foot (Control) | 2108.20 | 2235.20 | 127.00 |
| Right Foot (Test) | 2082.80 | 2260.60 | 177.80 |
| Mouse #6 | | | |
| Left Foot (Control) | 1981.20 | 2032.00 | 50.80 |
| Right Foot (Test) | 1981.20 | 2032.00 | 50.80 |

TABLE 15

EBV EBNA-1 - Second Test Population
(Only Transfer Factor Administered)

| | Footpad size (μm): | | |
|---|---|---|---|
| | Before Sample Injection (0 hrs.) | Final (24 hrs.) | Difference |
| Mouse #1 | | | |
| Left Foot (Control) | 2133.40 | 2159.00 | 25.40 |
| Right Foot (Test) | 2108.20 | 2159.00 | 50.80 |

TABLE 15-continued

EBV EBNA-1 - Second Test Population
(Only Transfer Factor Administered)

| | Footpad size (μm): | | |
|---|---|---|---|
| | Before Sample Injection (0 hrs.) | Final (24 hrs.) | Difference |
| Mouse #2 | | | |
| Left Foot (Control) | 2006.40 | 2032.00 | 25.40 |
| Right Foot (Test) | 1955.80 | 1955.80 | 0.00 |
| Mouse #3 | | | |
| Left Foot (Control) | 2032.00 | 2133.60 | 101.60 |
| Right Foot (Test) | 2006.60 | 2159.00 | 152.40 |
| Mouse #4 | | | |
| Left Foot (Control) | 2108.20 | 2133.60 | 25.40 |
| Right Foot (Test) | 2159.00 | 2159.00 | 0.00 |
| Mouse #5 | | | |
| Left Foot (Control) | 2184.40 | 2209.80 | 25.40 |
| Right Foot (Test) | 2159.00 | 2260.60 | 101.60 |
| Mouse #6 | | | |
| Left Foot (Control) | 2057.40 | 2108.20 | 50.80 |
| Right Foot (Test) | 2082.80 | 2133.60 | 50.80 |

Mean difference = 29.6

Student's t Test shows a 43% chance that means are not different.

| Mouse number | Right mouse pad for transfer factor plus vaccine (from Lisonbee table 14) | Right mouse pad for transfer factor alone (from Lisonbee table 15) |
|---|---|---|
| 1 | 25.40 | 50.80 |
| 2 | 25.40 | 0.00 |
| 3 | 152.40 | 152.40 |
| 4 | 101.60 | 0.00 |
| 5 | 177.80 | 101.60 |
| 6 | 50.80 | 50.80 |

VACCINATION RESPONSE FOR IMMUNODEFICIENCY OR HIGH CORTISOL

CROSS-REFERENCE TO RELATED APPLICATIONS

This application claims benefit of Ser. No. 13/877,309 filed Sep. 30, 2011 which claims benefit under 35 U.S.C. sctn.119(e) of U.S. Provisional Application No. 61/389,190, filed Oct. 1, 2010 and U.S. Provisional Application No. 61/389,230 filed Oct. 2, 2010, and for the United States is a continuation-in-part of U.S. application Ser. No. 12/631,745, filed Dec. 4, 2009. U.S. application Ser. No. 12/631,745, in turn, is a continuation of U.S. application Ser. No. 11/492,464, filed Jul. 24, 2006, which claims benefit under 35 U.S.C. .sctn.119(e) of U.S. Provisional Application No. 60/701,860, filed Jul. 22, 2005. U.S. application Ser. No. 11/492,464, in turn, is a continuation-in-part of U.S. application Ser. No. 11/106,054, filed Apr. 13, 2005, which claims benefit under 35 U.S.C. .sctn.119(e) of U.S. Provisional Application No. 60/573,113, filed May 20, 2004, and U.S. Provisional Application No. 60/649,363, filed Feb. 1, 2005. U.S. application Ser. No. 12/631,745 is also a continuation of U.S. application Ser. No. 11/237,316, filed Sep. 27, 2005, which is a division of U.S. application Ser. No. 10/136,854, filed Apr. 30, 2002, now U.S. Pat. No. 6,962,718, which is a continuation-in-part of U.S. application Ser. No. 09/847,036, filed Apr. 30, 2001, now U.S. Pat. No. 6,506,413. The disclosures of each of the foregoing patents and patent applications are incorporated herein entirely by reference.

STATEMENT REGARDING FEDERALLY SPONSORED RESEARCH

Not Applicable

REFERENCE TO A MICROFICHE APPENDIX

Not Applicable

BACKGROUND OF THE INVENTION

Field of the Invention

This invention relates to the treatment of humans with immunodeficiency disorders, who exhibit reduced or inadequate response to vaccines. More specifically, this invention describes method of consuming a medical food to activate the immune system before, during, or after vaccination. This enables the immune system to respond better, and produce a higher antibody immunity titer than would otherwise be achieved.

Description of Related Art

Immunodeficiency disorder refers to a heterogeneous group of over 130 disorders that result from defects in immune system development and/or function. Immunodeficiency disorders are broadly described as disorders of adaptive immunity (i.e., T-cell, B-cell or combination) or of innate immunity (e.g., phagocyte and complement disorders).

The population incidence of immunodeficiency disorders is difficult to quantify because many cases are not detected or treated. The person simply functions at a lower level, and repeatedly suffers from infections.

Although the clinical manifestations of immunodeficiency disorders are highly variable, most disorders involve at least an increased susceptibility to infection.

T cells and B cells are the primary cells of the adaptive immune system. B cells mediate antibody production and, therefore, play a major role in antibody-mediated immunity. Defects relating to B-cell development and/or maturation result in antibody-deficiency disorders.

T cells govern cell-mediated immune responses. Defects occurring at any stage of T-cell development, differentiation and maturation lead to T-cell (cellular) immunodeficiency disorders. Since B-cell-mediated antibody production requires intact T-cell function, most T-cell defects lead to combined (B- and T-cell) immunodeficiency disorders.

There are two generally recognized classes of immunodeficiency disorder: primary and secondary. Within this disclosure, we are defining a third class, which is high exposure immunodeficiency disorder.

Primary immunodeficiency disorder (PID) refers to a heterogeneous group of disorders characterized by poor or absent function in one or more components of the immune system. Most PIDs result from inherited defects in immune system development and/or function; however, acquired forms have also been described. Routine vaccinations at an early age may not work for a child with PID.

Secondary immunodeficiency disorder (SID) results from other causes. Examples include viral or bacterial infections, malnutrition, or treatment with drugs that induce immunosuppression. An excess of cortisol has been cited as a contributing factor.

High exposure immunodeficiency disorder (HEID) describes a situation wherein a person with a normal immune response is subjected to a high risk environment. Examples include medical students, hospital employees, and viral testing personnel. For these people, a high response titer is advantageous.

A person with any immunodeficiency disorder is in danger because he/she is vulnerable to opportunistic pathogens. The titer (which quantifies the level of immunity achieved by vaccination) may be well below normal. In some cases, the vaccination itself might cause a problem.

The treatment of immunodeficiency disorder is complex and generally requires both supportive and definitive strategies. Antibiotics and antifungals are commonly recommended for many immunodeficiency disorders to prevent the frequency and severity of infections.

The mainstay of therapy for most B-cell (antibody-deficiency) disorders is intravenous (IV) or subcutaneous Ig replacement therapy. Many patients will require this treatment indefinitely.

Vaccines are the primary tool to enhance the immune system. Vaccines present an inactivated antigen to the immune system, which then produces the appropriate protective antibodies. Vaccines are specific to a disease, but may be given in combination injections. Because the antigen is inactive, the process is safe.

Adjuvants are often used with a vaccine to stimulate the immune system. The only approved adjuvant in the United States is aluminum, which is a neurotoxin. The aluminum is present as an aluminum salt (such as aluminum hydroxide, aluminum phosphate, or aluminum potassium sulfate).

A superior way to activate stimulate the immune system would be a natural food, rather than a neurotoxin. A food-based adjuvant works to build the immune system, rather than just stimulate it.

There is a need for a medical food that builds immune function before, during, or after vaccination. The targeted response is a higher titer for persons with immunodeficiency disorders. A medical food can improve vaccine response with or without an aluminum adjuvant.

The potential for immune enhancement by transfer factor and lactic acid generating bacteria was first cited by Ramaekers [application Ser. No. 11/237,216, filed Sep. 27, 2005, full text version, paragraph 0180, line 1-2], which states, "In high risk cattle that are not preconditioned such as the heifers in these studies, direct stimulation of the immune system with stress formula along with vaccine administration appeared to indeed enhance the level of immunity against BRD."

BRIEF SUMMARY OF THE INVENTION

Following is a condensed summary of the current invention. By necessity, details are omitted in order to simply state the essence of the invention. Omitted details within this section should not be construed in a way that limits the scope of the invention.

The instant invention is a method of treating immunodeficiency disorders with a medical food that reduces human cortisol levels and simultaneously builds the immune system. By consuming the medical food, persons with immunodeficiency disorders can respond better to vaccinations. Hence, they are less susceptible to diseases.

Better immune response is quantified by measuring an antibody titer after vaccination. A higher titer indicates a higher level of immunity.

For persons traveling into less developed countries, a below average titer may cause anxiety. An above average titer provides a measure of comfort. Vaccine enhancement to achieve a better titer is a valid goal. That same logic applies to persons in hospitals and testing laboratories, where higher-than-normal exposure levels are expected.

The vaccine enhancement food that is used for the invented method contains at least transfer factor and lactic acid generating bacteria. A useful composition contains at least transfer factor, lactic acid generating bacteria, and glucans.

The invented method includes selecting the correct composition, choosing a dosage based on recipient weight, and deciding an appropriate consumption frequency.

Proof of vaccine enhancement is documented by animal studies. But the method-of-use for humans differs from the method-of-use for animals. All method claims presented contain elements that were first introduced by this disclosure.

BRIEF DESCRIPTION OF THE SEVERAL VIEWS OF THE DRAWINGS

FIG. 1 shows the increased vaccine response to parvo virus.

FIG. 2 shows the increased vaccine response to leptospirosis antigen.

FIG. 3 shows the cortisol response to transfer factor, lactic acid generating bacteria, and glucans during a calf study. The cortisol difference between test and control groups is significant at the 95% confidence level.

DETAILED DESCRIPTION OF THE INVENTION

This method-of-use invention utilizes a vaccine enhancement food based on transfer factor and lactic acid generating bacteria. In some embodiments, glucans are added.

Transfer factor, lactic acid generating bacteria, and/or glucans function synergistically to educate a host's own immune cells to react against an antigen. While transfer factor has been proven to build cellular immunity, studies have demonstrated that it does not influence the level of immunoglobulin in any significant way.

Transfer factors, which are produced by leucocytes and lymphocytes, are small water soluble polypeptides of between about 44 amino acids that stimulate or transfer cell mediated immunity from one individual to another and across species. Polypeptides below 10,000 Daltons comprise a useful weight fraction. Transfer factor from bovine colostrum extract has been defined as defatted water soluble material from colostrum that will pass through a nominal 10,000 molecular weight filter.

The properties, characteristics and processes for obtaining transfer factor or transfer factors are discussed in U.S. Pat. Nos. 4,816,563; 5,080,895; 5,840,700, 5,883,224 and 6,468,534, the contents of which are hereby incorporated by reference into the present application. A thorough discussion of transfer factor is included in Application Publication 20130243829, which is a priority document for the current application, and is incorporated entirely herein by reference. Some details about transfer factor will not be repeated here.

The transfer factor that is (1) used in the following recited study examples, (2) referred to in the following tables, and (3) further referred to in the rest of the detailed description is generally extracted from bovine colostrum or eggs. Bovine colostrum was collected from a general pool of lactating cows. It is well known to anyone skilled in the art that other kinds and sources of transfer factor could be used.

Alternative sources of transfer factor include, but are not limited to, avian transfer factor, ova transfer factor, and transfer factor isolated from colostrum collected from non-bovine animals such as goats, pigs, horses and humans. In addition, combinations of transfer factors from any number of sources may be used in the formulations of the instant invention. Transfer factor may also be derived from recombinant cells that are genetically engineered to express one or more transfer factors or by clonal expansion of leukocytes.

One of the specific effects of transfer factor is a significantly increased natural killer (NK) cell activity. Natural killer cells provide protection against viruses as part of the innate immune defense system. This effect is useful for vaccine enhancement. However, this invented vaccine enhancement method is not dependent on any specific effect or mechanism.

Lactic acid generating bacteria is an important component of the vaccine enhancement food. Foods such as cod liver oil and sauer kraut derive their benefit from lactic acid generating bacteria. The liver, pancreas, and kidneys are less stressed with good digestion.

Better intestinal bacterial balance contributes to better immunity. The immune system is supported because pathogens in the digestive tract are displaced by beneficial lactic acid generating bacteria. Healthy mucus intestinal linings are restored. Neither the invented vaccine enhancement food nor the method-of-use are limited to any particular biological mechanism. Support data for this invention is based on actual animal testing—not theory.

Lactic acid generating bacteria are generally recognized as safe (GRAS), and is often found in cheese.

Glucans are polysaccharides found in mushrooms. In some conversations, glucans and mushrooms are used interchangeably. Not all mushrooms are created equal. Hybrid mushrooms work better. If you were to start taking hybrid mushrooms every day, your immune capability could increase as much as 40%.

Glucans may be derived from multiple sources, including, but not limited to, fungi, oats, and yeast. Preferably, glucans are present in or derived from fungi. In certain embodiments, the glucans which may be included in the formulations are present in whole fungi. In certain preferred embodiments, glucans are present in or derived from *Cordyceps*, more preferably, *Cordyceps sinensis.*

In certain embodiments, glucans are derived from hybrid strains of fungi. In a preferred embodiment the hybrid glucans used in the invention are present in, or derived from, hybrid strains of *Cordyceps* and in particular *Cordyceps sinensis*. One technique to induce the hybridization of *Cordyceps* involves plating two different strains or species on a single agar plate which has been inoculated with rattlesnake venom as described in, for example, U.S. Patent Application Publication No. 2006/0073197, published Apr. 6, 2006, and U.S. Patent Application Publication No. 2007/0128253, published Jun. 7, 2007, each of which is incorporated herein by reference. In a preferred embodiment, the hybrid strain producing the hybrid glucans that may be used in compositions and formulations of the invention is *Cordyceps sinensis Alohaensis*, which is available from Pacific Myco Products, Santa Cruz, Calif.

In addition to *Cordycep sinensis* hybrids, suitable sources of glucans may include, but are not limited to, *Agaricus blazeii, Coriolus, Poira Cocos, Inonotus obliquus*, Maitake Mushroom, Shiitake Mushroom, and combinations thereof.

Equivalent amounts of purified or partially purified glucan as well as the nucleosides associated therewith (e.g., Cordycepin (3'deoxyadenosine), adenosine and N6-(2 hydroxyethyl)-adenosine) may also be used.

Combining transfer factor and lactic acid generating bacteria is synergistic, relative to enhancement immunity. The effect of the combination is greater than expected from either component alone. Combining transfer factor, lactic acid generating bacteria, and glucans is further synergistic.

In certain preferred embodiments, compositions may further comprise one or more of inositol hexaphosphate (Ip6), mannans, olive leaf extract, and phytosterols. In certain preferred embodiments, mannans are derived from Aloe vera. In certain preferred embodiments, phytosterols may be derived from soya bean.

In certain embodiments, compositions may further comprise one or more of lactic acid producing bacteria, ascorbic acid, Vitamin A, Vitamin D, Vitamin E, Vitamin B 1, Vitamin B2, Vitamin B12, dipotassium phosphate, potassium chloride, magnesium salts or chelates, and calcium pantothenate.

In certain embodiments, compositions and formulations comprising transfer factor may be combined with minerals, antioxidants, amino acids, and other nutraceuticals.

As stated above, the invented method utilizes the vaccine enhancement food to increase immunity before and after vaccination. The vaccine enhancement food also decreases the decay rate of immune response over time following vaccination, and prolongs the interval of time before re-vaccination (or a booster) is needed.

Projected economic benefits led to multiple method-of-use studies for vaccination of humans and animals. These studies disclosed previously unknown information.

In certain preferred embodiments, the formulation comprises transfer factor, lactic acid generating bacteria, and at least one glucan. In some embodiments, one or more additional ingredients are included. In certain embodiments, the transfer factor fraction may be lyophilized. In certain embodiments, the optional growth factor colostral fraction, other colostral fraction, antibody or antibody fraction may be lyophilized.

In some preferred vaccine enhancement food embodiments, active components are encapsulated by mixing with a hydrophobic substance or a lipid to form a coating around the transfer factor(s). In additional embodiments, one or more additional components including antibody, antibody fraction, growth factor fraction, other colostral fractions, and/or glucans may be encapsulated. Other optional components of compositions and formulations of the invention may be encapsulated, such as, without limitation, inositol hexaphosphate, olive leaf extract, mannans, phytosterol, vitamin C and mixtures thereof. The transfer factor, antibody or antibody fraction and/or additional optional components may each be individually encapsulated or encapsulated as a mixture. Alternatively, the entire formulation can be encapsulated. The encapsulated component(s) and/or formulation can be produced in a variety of ways. In a preferred embodiment, each of the transfer factor, lactic acid generating bacteria, glucans, antibody or antibody fraction and/or additional labile component(s) in the formulation may be encapsulated as described in U.S. Pat. Nos. 5,190,775, 6,013,286 and U.S. Application 2003/0129295, each of which is incorporated herein by reference in its entirety.

In certain embodiments, vaccine enhancement compositions and/or formulations may be administered to a subject orally. In additional embodiments, vaccine enhancement compositions and/or formulations may be administered to a subject by other suitable means, including, but not limited to, subcutaneously. In certain embodiments, transfer factor compositions and/or formulations may be administered to a subject parenterally.

In certain embodiments, vaccine enhancement compositions and/or formulations may be included in food. Preferred embodiments for human consumption include, but are not limited to incorporation of transfer factor formulations in processed foods such as cereals, snacks, chips, or bars.

In certain embodiments, oral or subcutaneous administration of a composition comprising transfer factor and lactic acid generating bacteria may be achieved by the use of a time-release or controlled-release implantable dosage form. Examples of suitable implantable dosage forms have been described in U.S. Pat. No. 5,665,363, U.S. Pat. No. 6,290,980, and RE 39,014 (a reissue of U.S. Pat. No. 6,290,980).

In certain embodiments, the invention relates to formulations that provide controlled (delayed) release of active agents. In certain embodiments, these formulations may be administered orally. In certain embodiments, the formulation may include a combination of water soluble and water insoluble polymers.

In certain embodiments, transfer factor, lactic acid generating bacteria, and glucans may be consumed at different times within a one week period.

In certain embodiments, one or more active agents are blended then compressed together with a combination of water soluble and water insoluble polymers to create a pill or a capsule.

In certain embodiments, the ingredients may be blended, then "slugged" on a tablet press. These slugs may be provided for inclusion in large gelatin capsules and delivered orally.

In another embodiment, the blends may have the powders compressed (densified) and fed en masse through a multiple orifice to make extruded strands that are cut with a blade to form small irregularly-shaped pellets.

In certain embodiments, the present invention provides methods for improving vaccine-induced immune response of the subject by administration of vaccine enhancement food. In particular embodiments, methods are provided for increasing the antibody response during and following vaccination. Antibody response is measured by determining the titer by laboratory testing. An example laboratory method is the rapid fluorescent focus inhibition test.

In certain aspects, methods according to the invention may be used to increase the duration of effective vaccine-induced immunity. This extends the time between initial vaccination and booster shots, while retaining effective protection against the targeted pathogen.

Preferably, the number of booster shots following initial vaccination of a subject against a specific pathogen is reduced to less than 4, less than 3, or less than 2. Preferably, the effective duration of antibody protection following vaccination is more than 1 year, more than 2 years or more than 3 years.

The number of subjects mounting an effective antibody response following administration of the invention before, during or after vaccination increases the vaccine efficacy rate by at least 5%, preferably at least 10%, and most preferably by at least 20%.

The following animal examples of vaccine enhancement are probative for humans also.

Examples of Vaccine Enhancement

Example 1

Effects of Transfer Factor on Post-Vaccinal Antibody Titer in Swine

This study shows the value of a vaccine enhancement food that is consumed following vaccination. Vaccine enhancement food may be consumed before, during, or after vaccination.

The study was undertaken to demonstrate the value of pure transfer factor derived from dairy colostrum and a formulation comprising transfer factor in titer enhancement. Later examples indicate that transfer factor combined with lactic acid generating bacteria or transfer factor combined with glucans performs even better for vaccine enhancement.

The vaccine tested was rabies vaccine IMRAB 3® (Lot number 12536b, available from Merial). Since pigs do not inherently carry a titer for rabies, the pigs would be expected to have immune systems naïve to this vaccine.

The study included 30 pigs, randomly selected 15 gilts (female) and 15 non-castrated male pigs ranging in age from 17 to 22 days. The animals were divided into three study groups of ten each, half female and half male. The pig groups were housed in individual pens after the study started.

Prior to the study, pigs were vaccinated at 10 days of age for mycoplasma, influenza, erysipelas and circo virus. All pigs were on the same pig starter diet (available from Sunglo) during this study.

On day 1 all pigs were bled, given 1 cc of Rabies vaccine subcutaneously and pigs were treated orally as described in TABLE 1, below. On day 1 and 21, serum was collected, and sent for testing at Kansas State Rabies Laboratory, Manhattan, Kans., where rabies titers were measured using a rapid fluorescent focus inhibition test.

TABLE 1

SWINE EXAMPLE-PROTOCOL

| PROTOCOL | Oral administration once on day 1 | Oral administration once daily, days 1 through 4 | Oral administration once daily, days 9, 14 and 19 |
|---|---|---|---|
| GROUP I (control) | 6 cc tap water | 6 cc tap water | 6 cc tap water |
| GROUP 2 (pure transfer factor derived from bovine colostrum) | 1 gram pure transfer factor in 6 cc tap water | 1 gram pure transfer factor in 6 cc tap water | 1 gram pure transfer factor in 6 cc tap water |
| GROUP 3 (Formulation A-Table 3) | 2 grams Form. A in 6 cc tap water | 2 grams Form. A in 6 cc tap water | 2 grams Form. A in 6 cc tap water |

Direct observations on day 21 of the study revealed that pigs treated with transfer factor in Groups 2 and 3 had the best appearance, even though three pigs from Group 3 started the study several pounds lighter or were younger pigs. Group 3 pigs, while still uneven in weight had the best coat and condition of all Groups. The control pigs lacked a show sheen or fullness of the transfer factor pigs from Groups 2 and 3.

The rapid fluorescent focus inhibition tests demonstrated increased titers in all Groups following initial titers <0.1 IU/ml, indicating that all pigs were naive to rabies antigens at the beginning of the study.

A chart providing results of rabies titer measurements is provided in TABLE 2, below.

TABLE 2

SWINE EXAMPLE-TITER RESULTS

| RESULTS | Average rabies titer prior to rabies vaccination | Average rabies titer 21 days following vaccination | Lowest Highest titer response | Number of pigs with no increase titer | Oral administration once daily, days 9, 14 and 19 |
|---|---|---|---|---|---|
| GROUP I (control) | <0.1 IU/ml | 2.87 IU/ml | <0.1 IU/ml 11.0 IU/ml | 3 | 6 cc tap water |
| GROUP 2 (pure transfer factor derived from bovine colostrum) | <0.1 IU/ml | 3.61 IU/ml | 0.5 IU/ml 13.0 IU/ml | 0 | 1 gram pure transfer factor in 6 cc tap water |
| GROUP 3 (Formulation A-Table 3) | <0.1 IU/ml | 5.55 IU/ml | <0.1 IU/ml >14.0 IU/ml | 1 | 2 grams Form. A in 6 cc tap water |

The average titer for the 10 pigs in the control-Group 1 was 2.87 IU/ml. It is common for pigs not to mount a an immune response to rabies vaccines. Not surprisingly, three of the pigs in Group 1 did not mount an immune response. Remarkably, all the Group 2 pigs and 90% of the Group 3 pigs mounted an immune response. In Group 2, pigs treated with pure transfer factor averaged 26% higher titer than in Group 1, at 3.61 IU/ml. Group 3 pigs were treated with Formulation A (TABLE 3, 4 below) and mounted the highest average immune response, averaging 12.31 IU/ml. One pig in Group 3 did not mount a response.

TABLE 3

FORMULATION A
2000 mg per dose:

| COMPONENTS | DESCRIPTION | PERCENTAGE |
|---|---|---|
| Transfer factor | Mammalian colostrum* and avian blend including avian antibodies | 38.4% |
| Inositol hexaphosphate | | 0.8% |
| Olive leaf extract | | 0.4% |
| Ace mannans | | 0.4% |
| Poly r plus | *cordyceps* hybrid, *cordyceps sinensis* extract, *cordyceps millitaris*, shitake, maitake, *innontus*, *obliquus*, *poira cocos*, *coriolus agaricus blazeii* extract. | 10.5% |
| *Cordyceps sinensis* extract | | 3.5% |
| *Agaricus blezei* | *cordyceps sinensis*, *grifola frondosa*, *ganoderma lucidum*, *coriolus versicolor lentinula edodes* blend 50% in the extract form and 50% non in extract form | 4.4% |
| Thymosine | | 4.4% |
| Vitamin E | | 5% |
| Zinc | | 1.7% |
| Electrolyte, vitamin blend with probiotics | | 28% |

*This colostrum blend indicated above contains higher molecular weight components including antibodies, praline-rich peptides, lactoferrin, growth factors in addition to the transfer factor filtrate.

TABLE 4

ELECTROLYTE, VITAMIN AND PROBIOTICS IN FORMULATION A/SERVING OF 2000 MG

| Ingredient | Amount per 2000 mg serving |
|---|---|
| Probiotics | 280 mg |
| Dibasic potassium | 350 mg |
| Citric acid | 95 mg |
| Dextrose | 4032 mg |
| Ascorbic acid | 7 mg |
| Sodium chloride | 448 mg |
| Magnesium sulfate | 22.4 mg |
| Calcium pantothenate | 5.6 mg |
| Vitamin A | 2.8 mg |
| Vitamin D3 | .308 mg |
| Riboflavin B2 | 3.58 mg |
| Vitamin B12 | 39.20 mg |
| Thiamine B1 | 3.36 mg |
| Yeast extract | 56 mg |
| Vitamin E | 2.46 mg |
| Potassium chloride | 56 mg |
| Glycine | 28 mg |

This study would indicate that Formulation A and transfer factor alone had a positive effect on vaccine response of rabies vaccination in swine compared to control. There was notable improvement in condition and weight performance of the treated pigs. See Table 5.

TABLE 5

DATA SWINE RABIES TITERS

| Patientl D | Draw Date | Titer IU/ml | DrawDate | Titer IU/ml |
|---|---|---|---|---|
| 6(248 | Jun. 21, 2010 | <0.1 | Jul. 12, 2010 | 3.7 |
| 1(242 | Jun. 21, 2010 | <0.1 | Jul. 12, 2010 | 3.7 |
| 7(251 | Jun. 21, 2010 | <0.1 | Jul. 12, 2010 | <0.1 |
| 2(256 | Jun. 21, 2010 | <0.1 | Jul. 12, 2010 | <0.1 |
| 3(246 | Jun. 21, 2010 | <0.1 | Jul. 12, 2010 | 6.3 |
| 10(222 | Jun. 21, 2010 | <0.1 | Jul. 12, 2010 | 11 |
| 4(285 | Jun. 21, 2010 | <0.1 | Jul. 12, 2010 | 1 |
| 8(252 | Jun. 21, 2010 | <0.1 | Jul. 12, 2010 | <0.1 |
| 9(223 | Jun. 21, 2010 | <0.1 | Jul. 12, 2010 | 2.2 |
| 5(243 | Jun. 21, 2010 | <0.1 | Jul. 12, 2010 | 0.5 |
| 8RB237 | Jun. 21, 2010 | <0.1 | Jul. 12, 2010 | 78.6 |
| 1RB2410 | Jun. 21, 2010 | <0.1 | Jul. 12, 2010 | 1.6 |
| 4RB241 | Jun. 21, 2010 | <0.1 | Jul. 12, 2010 | 8 |
| 7RB291 | Jun. 21, 2010 | <0.1 | Jul. 12, 2010 | 11 |
| 5R B233 | Jun. 21, 2010 | <0.1 | Jul. 12, 2010 | 1.8 |
| 9R B234 | Jun. 21, 2010 | <0.1 | Jul. 12, 2010 | 2.6 |
| 10RB232 | Jun. 21, 2010 | <0.1 | Jul. 12, 2010 | 2.6 |
| 2R B2510 | Jun. 21, 2010 | <0.1 | Jul. 12, 2010 | <0.1 |
| 3R B281 | Jun. 21, 2010 | <0.1 | Jul. 12, 2010 | 4.8 |
| 6R B292 | Jun. 21, 2010 | <0.1 | Jul. 12, 2010 | 12 |
| 2TF258 | Jun. 21, 2010 | <0.1 | Jul. 12, 2010 | 0.7 |
| 9TF221 | Jun. 21, 2010 | <0.1 | Jul. 12, 2010 | 2.6 |
| 1TF224 | Jun. 21, 2010 | <0.1 | Jul. 12, 2010 | 0.5 |
| 3TF283 | Jun. 21, 2010 | <0.1 | Jul. 12, 2010 | 2.6 |
| 8TF244 | Jun. 21, 2010 | <0.1 | Jul. 12, 2010 | 4.3 |
| 7TF247 | Jun. 21, 2010 | <0.1 | Jul. 12, 2010 | 4 |
| 5TF245 | Jun. 21, 2010 | <0.1 | Jul. 12, 2010 | 13 |
| 6TF253 | Jun. 21, 2010 | <0.1 | Jul. 12, 2010 | 0.5 |
| 10TF282 | Jun. 21, 2010 | <0.1 | Jul. 12, 2010 | 7 |
| 4TF231 | Jun. 21, 2010 | <0.1 | Jul. 12, 2010 | 0.9 |

Example 2

Effect of Parenteral Time-Release Transfer Factor on Rabies Titer Enhancement in Goats The effect of parenterally administered transfer factor and glucans was studied in a pair of twin goat bucklings. The addition of lactic acid generating bacteria would improve the effect.

One of the twins was administered a time-release pelleted transfer factor and a time-release pelleted hybrid *cordyceps* at the same time as the vaccination for rabies. The pellets containing transfer factor and glucans were injected on the second twin served as the control, receiving only rabies vaccination. 21 days after vaccination, the treated goat had a four-fold increase in rabies titer compared with the control.

Blood was taken from both 80 pound goats #227 (control) and #228 (treated) on day 1 followed by vaccination with 1 cc of IMRAB 3® subcutaneously and the following treatment in goat #228. 424 mg of active transfer factor wrapped with the time-release composition described in TABLE 6, below, was administered subcutaneously to goat #228 in eight pellets on the right side. 424 mg of actives comprising *cordyceps sinensis* hybrid wrapped with the time-release composition described in TABLE 6 was administered subcutaneously to goat #228 in eight pellets on the left side at the same time. No placebo was administered to goat #227. Feeding and housing of goats 227 and 228 were identical.

TABLE 6

| PURE TRANSFER FACTOR CONTROLLED-RELEASE FORMULATION | |
|---|---|
| Ingredient | Percent by weight |
| "Active" powder blend | 67.5% w/w |
| Hydroxypropyl cellulose (controlled release excipient) | 30.0% w/w |
| Calcium stearate (pelleting lubricant) | 2.0% w/w |
| Fumed silica (powder glidant) | 0.5% w/w |

Blood samples taken day one and 21 were tested for rabies titer using rapid fluorescent focus inhibition test. Titers increased from <1:5 in control goat #227 to 1:340; and from <1:5 to 1:1200 in treated goat #228. Results indicate an approximately 353% increase or a four-fold increase in rabies titer response for the study goat treated with time-release transfer factor and glucan extract.

Example 3

Effects of Transfer Factor on Vaccine Titers in Feedlot Cattle

Forty-four head of stockers, 500 pound feedlot cattle (approx. 200 days old) were tested for swine parvovirus and leptospirosis titers, following vaccination using vaccine manufactured for use in swine. The cattle were divided into 3 groups: one control group of 5 cattle and 20 cattle in Groups 2 and 19 cattle in Group 3, which were fed either immediate release oral transfer factor (see TABLE 7, below) or a combination of immediate and time-release oral transfer factor compositions (see TABLES 9, 10, 11, below). Following routine processing described in TABLE 8 the protocol described in TABLE 7 below, was utilized.

TABLE 7

FEEDLOT PROTOCOL

| PROTOCOL | # in group | Oral treatment | Days of treatment |
|---|---|---|---|
| Group 1 (Control) | 5 | | |
| Group 2 immediate release formula | 20 | One gelatin capsule containing 0.83 oz of TABLE 4 formula | Day 1, 2 and 12 |
| Group 3 immediate release formula plus time-release formula | 19 | One gelatin capsule containing 0.83 oz of TABLE 4 and two gelatin capsules of TABLE 6 & 7 formula | Day 1 and 12 |

TABLE 8

PROCESSING OF CATTLE PRIOR TO EXPERIMENT

| DATE | PROCEDURE |
|---|---|
| Oct. 7, 2009 | Cattle Delivered |
| | Tagged and grouped<br>All vaccinated for: Infectious Bovine Rhinotracheitis (IBR), Parainfluenza virus (PI3), Bovine Viral Diarrhea (BVD), Bovine Respiratory Syncytial Virus (BRSV)*<br>ST-BAC** implant, dewormed, treated for ectoparasites |

*Note:
100% of the cattle were subsequently diagnosed with positive titers indicating BRSV infection; 40% infection with BVD and 40% infection with PI3.
**vaccine for *Histophilus somni*, *Mannheimia*, *Haemolytica*, *Mycoplasma bovis*, *Pasteurella multocida*

TABLE 9

TRANSFER FACTOR LIVESTOCK STRESS RUMEN BY-PASS FORMULATION**
Amounts in mg/lb of body weight unless otherwise stated Stabilized components*

| Ingredient | Amount: mg/oz (unless otherwise noted) of formula |
|---|---|
| Transfer factor (mammal source)* | 3500.0 |
| Transfer factor (avian source)* | 1000.0 |
| P-sitosterol (90% phytosterols)* | 300.0 |
| Inositol hexaphosphate* | 350.0 |
| Olive leaf extracts* | 35.0 |
| Aloe extract powder* (200:1) | 17.0 |
| Hybridized and non-hybridized Glucans* (from Hybridized *Cordyceps sinensis*, *Agaricus blazeii*, Miatake, Shitake, *Coriolis*, *Inonotus*, *Obliquus*, and *Poris cocos* mushrooms) | 4000.0 |
| Vitamin C* | 2000.0 |
| Vitamin A | 4434 IU/oz |
| Vitamin D3 | 1140 IU/oz |
| Vitamin E | 500 IU/oz |
| Vitamin B1 | 12.77 |
| Vitamin B2 | 12.77 |
| Vitamin B12 | 1.5 |
| Di-potassium phosphate | 1.5 g/oz |
| Potassium chloride | 207 |
| Magnesium sulfate | 83 |
| Calcium pantothenate | 23 |
| Ascorbic acid | 23 |
| Lactic acid bacteria | $2.5 \times 10^{11}$ CFU/oz |
| Yeast (*S. cerevisiae*) | $15.0 \times 10^{6}$ CFU/oz |
| Zinc proteinate | 10 |

*Stabilized active ingredients are included in a formulation of 50% soybean oil and 50% active ingredient.

TABLE 10

ACTIVE BLEND (PER SERVING)

| INGREDIENT | AMOUNT |
|---|---|
| Mammalian transfer factor blend (transfer factor, antibodies, high molecular weight colostral fraction) | 5103 mg |
| Avian transfer factor | 773 mg |
| IP6, olive leaf extract, acemannan, phytosterol | 644 mg |
| PolyR | 3289 mg |
| Porcine thymosin | 1610 mg |

TABLE 11

TIME-RELEASE FORMULATION
Once Active blend is coated with formulation below, the composition is formed into pellets. These pellets are placed inside gelatin capsules (size 7) for oral administration.

| INGREDIENT (Function) | AMOUNT |
|---|---|
| Active powder blend from Table 6 | 50% w/w |
| Ethylcellulose (filler and controlled release polymer) | 39.5% w/w |
| Hydroxypropyl cellulose (binder and pore-former) | 8.0% w/w |
| Stearic acid (pelleting lubricant) | 2.0% w/w |
| Fumed silica (Powder glidants) | 0.5% w/w |

Cattle in Groups 2 and 3 showed three times the rate gain as the controls, and had a 220% increase in titer to both swine parvovirus and leptospirosis. 100% of the control group had no response to leptospirosis vaccination at day 21, while 90% from Group 2 and 89% from Group 3 had titers at day 21, which remained stable or increased by day 42 in 61% of Group 2 and 65% of the Group 3 responders as demonstrated in Table 12, below. Response to parvovirus vaccine was equally unexpected in the treated Groups as compared to the controls. Group 2 and 3 mounted a 4.5 and 5 times greater immune antibody titer response to the leptospirosis vaccine than controls, respectively; and a 3.2 and 4.6 times greater titer response to parvo virus vaccine than controls. Notably, there was significantly slower vaccine decay in both treated groups compared with controls.

In addition to the direct immune modulating response, the Group 2 and 3 cattle averaged 3.17 and 2.78 pounds of weight gain per day by day 42 compared with only 1.51 pounds of weight gain per day in the control group. Notably, there were no side effects in the treated cattle groups to the swine vaccines.

TABLE 12

SUMMARY OF COMPARED TITER RESPONSE IMMUNO MODULATION TO INCREASE ANTIBODY TITER RESPONSE

| | C-LIT | RB-LIT | RBTF-LIT |
|---|---|---|---|
| O DAY | <100/neg | <100/neg | <100/neg |
| 21 D | <100/neg | 200.0:1 | 263.0:1 |
| 42 D | <100/neg | 190.0:1 | 174.0:1 |
| | C-PVT | RB-PVT | RBTF-PVT |
| O DAY | 46/neg | <16/neg | <16/neg |
| 21 D | 80.0:1 | 259.0:1 | 368.0:1 |
| 42 D | 2.2:1 | 239.0:1 | 273.0:1 |

CONTROL = C (N = S)
RUMEN BY-PASS = RB (N = 19)
RUMEN BY-PASS -TIME RELEASE = RBTF (N = 20)
LEPTO ICTERO TITRE = LIT
PARVO VIRUS TITRE = PVT
*titres are mean values of the group.

Table 13 has been omitted. Data is presented in FIG. 1.
Table 14 has been omitted. Data is presented in FIG. 2.

TABLE 15

CONTROL GROUP DATA
CONTROLS

| TAG | O DAY WT | 21 D WT | 42 D WT | #GAINED | ADG | O D LEP | 21 D LEP | 42 D LEP | ICTERO | O D PPV | 21 D PPV | 41 D PPV |
|---|---|---|---|---|---|---|---|---|---|---|---|---|
| 9-056 | 592 | 656 | | | 3.04 | <100/NEG | <100/NEG | | | <16/NEG | 64/* | |
| 9-058 | 586 | 650 | | | 3.01 | <100/NEG | <100/NEG | | | 32/* | 256/* | |
| 9-057 | 532 | 548 | | | 0.76 | <100/NEG | <100/NEG | | | <16/NEG | 64/* | |
| 9-052 | 477 | 453 | | | LOSS 24 # | <100/NEG | <100/NEG | | | 16/* | 32/* | |
| 9-049 | 474 | 499 | | | 1.19 | <100/NEG | <100/NEG | | | <16/NEG | 64/* | |
| | | AV: 29# | | | | | AV. 1.6 | | | | AV 2:1 | |

TABLE 16

GROUP 2 DATA

| TREATSRB | TAG | O DAY WT | 21 D WT | 42 D WT | # GAINED | ADG | O D LEP | 21 D LEP | 42 D LEP | ICTERO | O DA PPV | 21 D PPV | 42 D PPV |
|---|---|---|---|---|---|---|---|---|---|---|---|---|---|
| | 9-001 | 436 | 520 | 622 | 186 | 4.42 | <100/NEG | 100/* | 100/* | | 32/* | 512/* | 32/* |
| | 9-011 | 494 | 596 | 620 | 126 | 3 | <100/NEG | 400/* | 200/* | | <16/NEG | 16/* | 200/* |
| | 9-053 | 460 | 564 | 650 | 190 | 4.52 | <100/NEG | 200/* | 200/* | | 16/* | 256/* | 256/* |
| | 9-015 | 411 | 457 | 484 | 73 | 1.74 | <100/NEG | <100/NEG | <100/NEG | | 32/* | 16/* | 64/* |
| | 9-017 | 452 | 499 | 560 | 108 | 2.57 | <100/NEG | 200/* | 200/* | | 16/* | 256/* | 256/* |
| | 9-019 | 473 | 508 | 586 | 113 | 2.69 | <100/NEG | 400/* | 800/* | | <16/NEG | 128/* | 256/* |
| | 9-051 | 365 | 437 | 452 | 87 | 2.07 | <100/NEG | 100/* | 100/* | | <16/NEG | 64/* | 100/* |
| | 8-023 | 398 | 397 | 432 | 34 | 0.81 | <100/NEG | 100/* | 100/* | | <16/NEG | 512/* | 100/* |
| | 9-055 | 449 | 554 | 670 | 221 | 5.26 | <100/NEG | 400/* | 200/* | | <16/NEG | 256/* | 512/* |
| | 9-061 | 432 | 499 | 550 | 118 | 2.8 | 100/* | 200/* | 100/* | | 128/* | 256/* | 64/* |
| | 9-029 | 340 | 394 | 497 | 157 | 3.74 | <100/NEG | 200/* | 100/* | | 16/* | 32/* | 100/* |
| | 9-031 | 385 | 470 | 522 | 137 | 3.26 | <100/NEG | 100/* | <100/NEG | | <16/NEG | 128/* | 64/* |
| | 9-033 | 423 | 499 | 552 | 120 | 2.86 | <100/NEG | 100/* | 100/* | | <16/NEG | 512/* | 256/* |
| | 9-035 | 407 | 530 | 594 | 187 | 4.45 | <100/NEG | 100/* | 200/* | | 32/* | 128/* | 256/* |
| | 9-037 | 346 | 421 | 508 | 162 | 3.86 | <100/NEG | 400/* | 100/* | | 32/* | 256/* | 512/* |
| | 9-039 | 351 | 384 | 397 | 46 | 109 | <100/NEG | 200/* | 100/* | | <16/NEG | 1024/* | 512/* |
| | 9-041 | 406 | 492 | 532 | 126 | 3 | <100/NEG | 200/* | 800/* | | <16/NEG | 256/* | 512/* |
| | 9-043 | 424 | 517 | 602 | 178 | 4.24 | <100/NEG | 200/* | 200/* | | <16/NEG | 256/* | 512/* |
| | 9-045 | 428 | 552 | 614 | 186 | 4.43 | <100/NEG | 100/* | 200/* | | <16/NEG | 256 | 200/* |
| | 9-047 | 375 | 417 | 481 | 106 | 2.53 | <100/NEG | <100/NEG | <100/NEG | | <16/NEG | 32/* | 16/* |
| | | AV: 413# | AV: 72.5# ADG: 3.45# | | AV: 133# | ADG: 3.17# | | | | | | | |

TABLE 17

| GROUP 3 DATA | | | | | | | | | | | | | |
|---|---|---|---|---|---|---|---|---|---|---|---|---|---|
| TREATSRB-TR | TAG | O DAY WT. | 21 D WT | 42 D WT | # GAINED | ADG | O D LEP | 21 D LEP | 42 D LEP | ICTERO | O DA PPV | 21 D PPV | 42 D PPV |
| | 9-054 | 423 | 522 | 542 | 119 | 2.83 | <100/NEG | 8001* | 400/* | | 32/* | 128/* | <16/NEG |
| | 9-012 | 327 | 402 | 414 | 87 | 2.07 | <100NEG | 200/* | 400/* | | 32/* | 128/* | 400/* |
| | 9-014 | 469 | 576 | 652 | 183 | 4.35 | <100/NEG | 200/* | 200/* | | 16/* | 256/* | 64/* |
| | 9-016 | 458 | 552 | 598 | 140 | 3.3 | <100/NEG | 100/* | 400/* | | 16/* | 256/* | 128/* |
| | 9-018 | 445 | 498 | 516 | 71 | 1.69 | <100/NEG | <100/NEG | <100/NEG | | 16/* | 64/* | 64/* |
| | 9-020 | 335 | 391 | 424 | 89 | 2.11 | <100/NEG | 200/* | 100/* | | <16/NEG | 256/* | 256/* |
| | 9-024 | 329 | 383 | 423 | 94 | 2.23 | <100/NEG | 200/* | 200/* | | 16/* | 256/* | 64/* |
| | 9-026 | 395 | 510 | 568 | 173 | 4.11 | <100/NEG | 100/* | 100/* | | 2048/* | 2048/* | 2048/* |
| | 9-028 | 450 | 560 | 610 | 160 | 3.81 | <100/NEG | 8001* | 100/* | | 16/* | 32/* | 32/* |
| | 9-030 | 388 | 418 | 436 | 48 | 1.14 | <100/NEG | 400/* | 100/* | | <16/NEG | 512/* | 512/* |
| | 9-032 | 386 | 456 | 546 | 160 | 3.81 | <100/NEG | <100/NEG | <100/NEG | | 32/* | 128/* | 128/* |
| | 9-034 | 427 | 467 | 476 | 49 | 1.16 | <100/NEG | 200/* | 100/* | | <16NEG | 512/* | 100/* |
| | 9-036 | 466 | 574 | 614 | 148 | 3.52 | <100/NEG | 100/* | 100/* | | <16/NEG | 256/* | 256/* |
| | 9-038 | 431 | 538 | 622 | 191 | 4.54 | <100/NEG | 400/* | 200/* | | 32/* | 512/* | 16/* |
| | 9-050 | 320 | 414 | 495 | 175 | 4.16 | <100/NEG | 100/* | 100/* | | <16/NEG | 1024/* | 512/* |
| | 9-066 | 449 | 546 | 606 | 157 | 3.74 | 8001* | 8001* | 200/* | | <16NEG | 32/* | 200/* |
| | 9-044 | 423 | 546 | 620 | 197 | 4.69 | <100/NEG | 100/* | 200/* | | <16/NEG | 32/* | 200/* |
| | 9-046 | 380 | 434 | 453 | 73 | 1.73 | <100/NEG | 100/* | 200/* | | <16/NEG | 512/* | 200/* |
| | 9-048 | 413 | 532 | 586 | 173 | 4.11 | <100/NEG | 200/* | 100/* | | <16/NEG | 64/* | 16/* |
| | | | AV: 82# ADG: 3.92# | | AV: 117# | ADG: 2.78# | | | | | | | |

Example 4

Effect of Transfer Factor Administer Orally to Cats During and Following Rabies Vaccination A cat 20 years old, when titer for rabies was attempted, was essentially negative for two titers (e.g., titers of approximately 0.17 IU/mL), having been given rabies vaccination three consecutive years. After administration of the transfer factor formulation (see TABLE 18, below) one tsp daily in drinking water for several weeks, and 0.15 cc of rabies vaccine or 15% of a standard dose, the rabies titer was raised to approximately 1.52 IU/mL.

TABLE 18

TRANSFER FACTOR FORMULATION (NO ENCAPSULATION)
(Amounts in mg/lb of body weight unless otherwise stated)

| Component | High | Low | Preferred | Dosage: mg/oz of formula |
|---|---|---|---|---|
| Calcium Pantothenate | 1.80 | 0.09 | 0.028 | 28.00 |
| Vitamin C (ascorbic acid) | 20.00 | 0.056 | 0.017 | 17.00 |
| Vitamin $B_{12}$ | 13.00 | 0.13 | 0.198 | 198.59 |
| Vitamin A | 600.00 IU | O.IO IU | 0.014 | 14.00 |
| Vitamin $B_2$ | 1.20 | 0.065 | 0.018 | 18.00 |
| Thiamine | 16.00 | 0.0308 | 0.017 | 17.00 |
| Vitamin E | 72.9 IU | 0.729 IU | 0.012 | 12.48 |
| Magnesium Sulfate | 10.00 | 0.113 | 0.113 | 113.00 |
| **Lactobacillus acidophilus* ($10^9$ colony forming units (CFU)/gm) | 10.00 | 0.467 | 1.418 | 1418.00 |
| Sodium Chloride | 166.00 | 0.236 | 2.368 | 2368.00 |
| Dipotassium phosphate | 116.00 | 5.85 | 1.773 | 1773.00 |
| Citric acid | 31.00 | 1.59 | 0.482 | 482.00 |
| Yeast (hydrolyzed) | 180.00 | 0.1957 | 0.283 | 283.00 |
| Glycine | 0.142 | 0.0142 | 0.142 | 141.80 |
| Potassium chloride | 18.00 | 0.93 | 0.283 | 283.00 |
| Vitamin D3 | 29.00 | 0.729 | 0.002 | 1.56 |
| Dextrose | 40.00 | 2.00 | 21.38 | 21375.00 |
| Artificial flavor | 0.028 | 0.0028 | 28.548 | 28.30 |

TABLE 18-continued

TRANSFER FACTOR FORMULATION (NO ENCAPSULATION)
(Amounts in mg/lb of body weight unless otherwise stated)

| Component | High | Low | Preferred | Dosage: mg/oz of formula |
|---|---|---|---|---|
| Transfer Factor | 50.00 | 0.05 | 0.75 | 750.00 |
| Sipernat (silicon dioxide) | | | 0.05 | 56.70 |

A 19 week old kitten was administered rabies vaccination, 1 cc IMRAB 3® subcutaneously following a test for rabies titer revealing a titer of <1 UL/ml, considered a negative titer. The kitten was fed 1500 mg. transfer factor in a chew formulation daily for 42 days. 21 days later the kittens rabies titer was greater than 14 IU/ml and by day 42 it increased to 15 IU/ml. The administration of transfer factor with and following vaccination unexpectedly boosts the immune response for a prolonged time period.

It will be apparent to those skilled in the art that various modifications and variations can be made in the methods and compositions of the present inventions without departing from the spirit or scope of the invention. Thus, it is intended that the present invention cover the modification and variations of the inventions provided they come within the scope of the appended claims and their equivalents.

The terms and expressions which have been employed are used as terms of descriptions and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope on this invention.

In addition, where features or aspects of the invention are described in terms of Markush group or other grouping of alternatives, those skilled in the art will recognized that the invention is also thereby described in terms of any individual member or subgroup of members of the Markush group or other group.

Unless indicated to the contrary, all numerical ranges described herein include all combinations and subcombinations of ranges and specific integers encompassed therein. Such ranges are also within the scope of the described invention.

The disclosures of each patent, patent application and publication cited or described in this document are hereby incorporated herein by reference, in their entirety.

For application as a human medical food, the vaccine enhancement food may be consumed prior to vaccination, consumed during the vaccination, or consumed after the vaccination. It is understood that these time periods may be combined. For example, vaccine enhancement food might be consumed before, during and after vaccination.

One preferred method is consumption of the vaccine enhancement food 3 to 60 days before vaccination. Early consumption allows a person's overall immune system to strengthen. When the inactivated antigen is presented in the vaccine, the immune system is in an advantageous state to respond. Of course, consumption more than 60 days prior to vaccination may be appropriate for some humans.

Another preferred method is consumption of vaccine enhancement food following vaccination. Post-vaccination consumption can lead to increasing titers long after the anticipated response is achieved. In one example, the rabies titer for a cat continued to increase between day 21 and day 42 following the vaccination. Instead of decaying, the titer increased.

Another preferred method is to start the vaccine enhancement food at the time of vaccination. In most cases, this will be coupled with post-vaccination consumption.

Dosages and feeding frequencies differ between animals and humans. This is particularly true for livestock animals, where feeding schedules are not flexible. Feeding frequencies for livestock are chosen based on economics rather than efficiency. Feeding dosages are set for the herd, not the individual cow or pig. It is unlikely that the herd's feeding schedule and frequency will be changed for one animal.

Feeding frequencies for humans are chosen based on efficiency, and are flexible. Dosage levels and feeding frequencies can be adjusted based on individual responses. Feedback from testing laboratories is useful to modify both dosage levels and feeding frequencies. The relative proportions of transfer factor, lactic acid generating bacteria and glucans within each dosage can be optimized.

Dosages of vaccine enhancement food are chosen on a person's weight. Dosage levels are derived from both animal and human data.

With human variations understood, a reasonable weight range for transfer factor in a vaccine enhancement food is 0.05-50 mg per pound of body weight. A reasonable weight range for lactic acid generating bacteria in a vaccine enhancement food 0.47-10 mg per pound of body weight, based on a nominal live count of 1.5-3.5 million CFU/ounce (colony-forming-units-per-ounce). A reasonable weight range for glucans in a vaccine enhancement food is 0.1-10 mg per pound of body weight.

These ranges allow for latitude in proportions of ingredients used within a vaccine enhancement food.

For some patients, transfer factor, lactic acid generating bacteria, and glucans are taken together. For other patients, transfer factor, lactic acid generating bacteria, and glucans are taken at different times during the day or week. Component separation and consumption at different times are within the scope of this invention. Separate consumption and was recited in Ramaekers' U.S. Publication 20070128253, which benefits this application. The human body performs the mixing.

Optimal consumption frequencies of the vaccine enhancement food vary between five times per day and once per week. When transfer factor, lactic acid generating bacteria, and glucans are taken at different times, the consumption frequency of each component is between five times per day and once per week.

The literature recites a connection of poor immune response to high cortisol levels. Cortisol is the body's major stress hormone. For example, persons being medically treated with cortisol often show reduced immune response. If a person exhibits high cortisol levels, the probability of vaccine enhancement is further supported. The reason is that the vaccine enhancement food also reduces cortisol levels.

A method of using the vaccine enhancement food may have some or all of the following steps: (1) select the correct proportion of transfer factor, lactic acid generating bacteria, and glucans for the vaccine enhancement food, (2) choose a correct dosage level based on a person's weight, (3) choose a correct dosage level based on a person's prior vaccine response history, (4) select a consumption frequency between five times per day and once per week, (5) decide whether the components of the vaccine enhancement food will be administered at same time or separately, (6) consume the vaccine enhancement food 3-30 days prior to vaccination, (7) begin consumption of the vaccine enhancement food at the time of vaccination, (8) continue consumption of the vaccine enhancement food for 60 days after vaccination, (9) continue consumption of the vaccine enhancement food beyond 60 days to maximize the period of immunity, (10) measure killer T-cell count and adjust the dosage or consumption frequency of the vaccine enhancement food, (11) measure antibody titers and adjust the dosage or consumption frequency of the vaccine enhancing food, (12) measure cortisol levels before vaccination, (13) increase the dosage or consumption frequency of vaccine enhancement food for person's travelling abroad to high risk countries, (14) increase the dosage or consumption frequency of vaccine enhancement food for person's working in high exposure professions, (15) reduce the initial dosage level for long term titer maintenance, (16) using a booster vaccination within 120 days of the first vaccination, and (17) monitor progress through a health care professional.

A composition of transfer factor and lactic acid generating bacteria was patented by Joseph Ramaekers (a current joint inventor). Refer to U.S. Pat. No. 6,962,718, claim 6, issued Nov. 8, 2005, which recites, "A formulation comprising pharmaceutically acceptable transfer factor and a pharmaceutically acceptable lactic acid generating bacteria wherein the amount of said transfer factor is from 10 mg to 10,000 mg per ounce of formulation".

The method of using transfer factor, lactic acid generating bacteria, and glucans for vaccine enhancement can also be viewed as two improvements to U.S. Pat. No. 6,962,718. The two improvements (limitations) are (1) the addition of glucans, to the patented formulation, and (2) the specific method of using the patented formulation to enhance immune response to vaccination. Improvement claims are presented in the claims section.

Vaccine enhancement may be applied to *bordetella pertussis, haemophilus influenzae* b, *neisseria meningitides*, poliovirus, *streptococcus pneumoniae*, tetanus toxoid, diphtheria toxoid, and rabies virus, polio, measles, mumps, rubella, and human papillomavirus. This listing cites examples, and is not a complete list of applications.

Minor variations on this disclosure remain within the scope of this disclosure.

We claim:

1. A method of increasing the antibody production of a vaccine for a human with a formulation, comprising:

preparing the formulation, wherein said formulation comprises at least transfer factor and lactic acid generating bacteria, wherein said transfer factor in each dosage is present at 0.05 to 50 mg per pound of said human's body weight, and said lactic acid generating bacteria in each said dosage is present at 0.47-10 mg per pound of said human's body weight;

incorporating said formulation into a solution for injection, into a food for consumption, or into a liquid for consumption; and administering the formulation to said human before, during, or after the vaccine is administered, wherein more antibodies are created by the vaccine plus formulation than are created by the vaccine without the formulation.

2. The method of claim 1 further comprising measuring a vaccine antibody titer to quantify said increasing.

3. The method of claim 2 wherein said antibody titer is specific to any one disease selected from the group consisting of *bordetella pertussis, haemophilus influenzae* b, *neisseria meningitides*, poliovirus, *streptococcus pneumoniae*, tetanus toxoid, diphtheria toxoid, rabies virus, polio, measles, mumps, rubella, and human papillomavirus.

4. The method of claim 2 wherein said measuring of said vaccine antibody titer is performed 10-60 days after administration of said vaccine.

5. The method of claim 1 wherein said formulation further comprises one or more additives selected from the group consisting of glucans, hetero-polysaccharides, vitamins, electrolytes, probiotics, and immune modulators.

6. The method of claim 5 wherein said glucans are derived from mushrooms or hybrid mushrooms.

7. The method of claim 5 wherein said glucans are present at 0.05 to 50 mg per pound of said human's body weight.

8. The method of claim 1 wherein said administering occurs 3-30 days before said vaccine is administered.

9. The method of claim 1 wherein said administering continues between five times per day and once per week for 1 to 60 days after said vaccine is administered.

10. The method of claim 9 wherein said administering continues after said 60 days.

11. The method of claim 1 further administering a booster vaccine that is given within 120 days of the first vaccine.

* * * * *